US00PP14950P2

(12) United States Plant Patent
Pieters

(10) Patent No.: US PP14,950 P2
(45) Date of Patent: Jun. 29, 2004

(54) CHRYSANTHEMUM PLANT NAMED 'GEDI TWO AMA'

(50) Latin Name: *Chrysanthemum morifolium*
Varietal Denomination: Gedi Two Ama

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/613,718

(22) Filed: Jul. 3, 2003

(51) Int. Cl.[7] ..... A01H 5/00
(52) U.S. Cl. ..... Plt./291
(58) Field of Search ..... Plt./291, 287, 292

(56) References Cited

U.S. PATENT DOCUMENTS

| | | |
|---|---|---|
| PP11,855 P2 | 5/2001 | Glicenstein |
| PP13,689 P3 | 4/2003 | Pieters |
| PP13,891 P3 | 6/2003 | Pieters |

*Primary Examiner*—Anne Marie Grunberg
*Assistant Examiner*—Annette H Para
(74) *Attorney, Agent, or Firm*—Knobbe, Martens, Olson & Bear LLP

(57) ABSTRACT

A new and distinct Chrysanthemum plant cultivar is disclosed, characterized by a spider type flower form having pink/purple ray florets. The new variety is a garden type chrysanthemum, and naturally blooms about the first week of September.

1 Drawing Sheet

Figure 1:
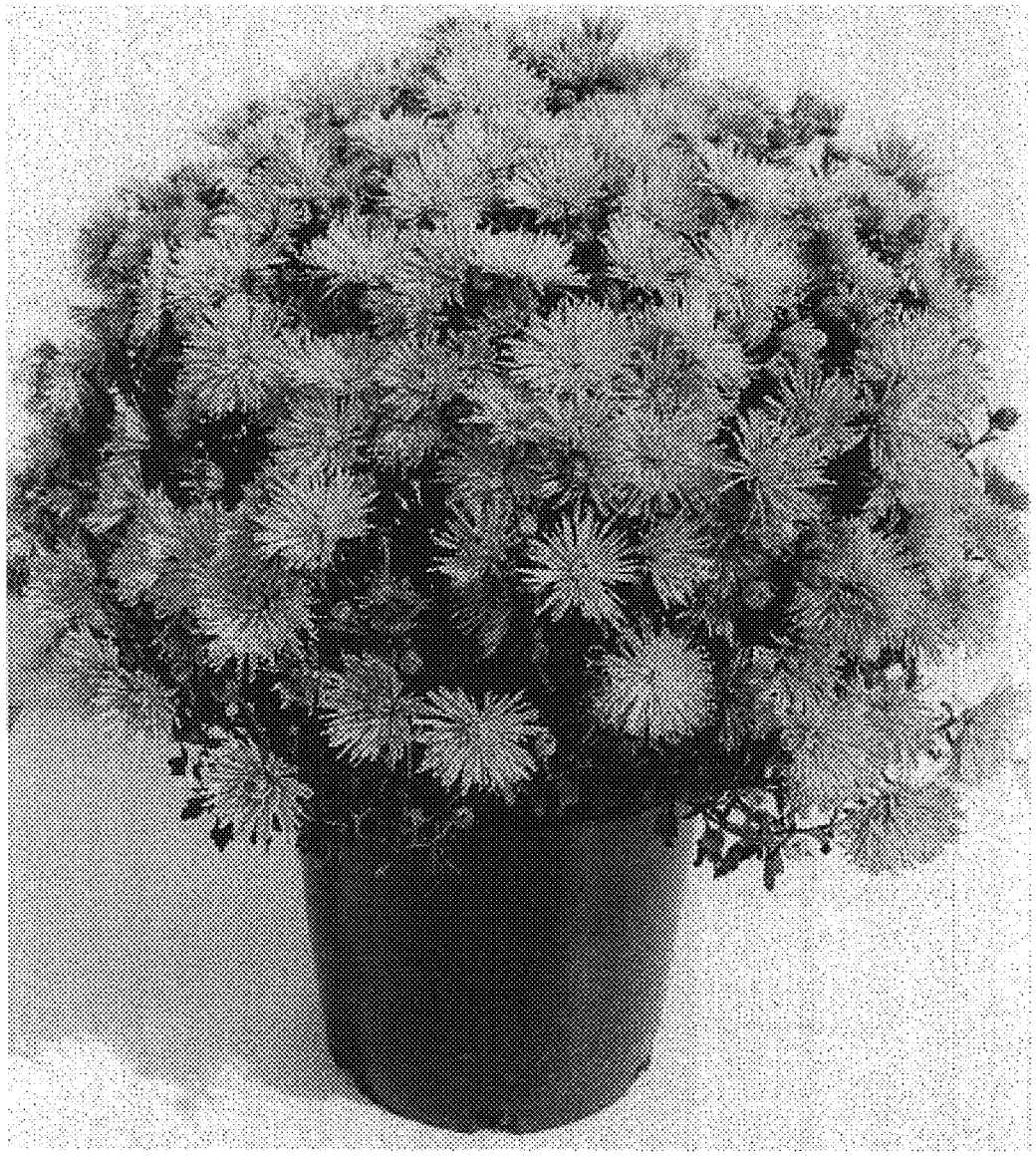

Latin name of the genus and species: *Chrysanthemum morifolium.*
Variety denomination: 'Gedi Two Ama'.

BACKGROUND OF THE INVENTION

The present invention relates to a new and distinct cultivar of garden-type Chrysanthemum plant, herein after referred to by the cultivar name 'Gedi Two Ama'. The new cultivar is a product of induced mutation and selection of an unpatented cultivar called 'Amandola.' Mutation of 'Amandola' was induced by irradiation of unrooted cuttings. The selection from the irradiated cuttings was made by Dirk Pieters in September 2001.

Asexual reproduction of the new cultivar by vegetative cuttings and tissue culture was performed in Staden, Belgium and in Oxnard, Calif., and has shown that the unique features of this cultivar are stable and reproduced true to type on successive generations.

SUMMARY OF THE INVENTION

The cultivar 'Gedi Two Ama' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Ged Two Ama.' These characteristics in combination distinguish 'Gedi Two Ama' as a new and distinct Chrysanthemum cultivar:

1. Garden type Chrysanthemum.
2. Pink/purple ray florets.
3. Spider type flower form.

Plants of the new variety are similar to plants of the source cultivar from which the new variety was derived, 'Amandola,' in most horticultural characteristics. However, plants of the new cultivar are taller and have a larger diameter inflorescense than plants of the 'Amandola' cultivar. Additionally, the new variety produces more lateral branches, and also produces more flowers per lateral branch than the 'Amandola' cultivar. 'Amandola' was made by hybridization of a female parent Chrysanthemum plant variety 'Gedi Two Tar' (U.S. Plant Pat. No. 13,689) and a male parent Chrysanthemum plant variety 'Gedi One Jam' (U.S. Plant patent application Ser. No. 09/863,748), which was performed in September, 1997 by Dirk Pieters. Multiple generations of the resulting 'Amandola' cultivar were reproduced and flowered. In January 1999 unrooted cuttings of the cultivar 'Amandola' were irradiated, selected, and propagated, producing the final cultivar described in this application.

Plants of the new cultivar are similar to plants of the female grandparent variety, 'Gedi Two Tar' in most horticultural characteristics, however plants of the new cultivar have pink/purple ray florets, in contrast to the yellow ray florets of the female parent variety 'Gedi Two Tar'. Additionally, plants of the new cultivar are taller and have a larger diameter inflorescence than plants of the female parent variety, 'Gedi Two Tar'. Further, the new variety blooms approximately two weeks earlier than 'Gedi Two Tar.'

Plants of the new cultivar are similar to plants of the male grandparent variety, 'Gedi One Jam' in most horticultural characteristics. However, plants of the new cultivar have a spider-type bloom while the male parent variety, 'Gedi One Jam' has a decorative-type bloom. The new variety has a smaller diameter inflorescence than does 'Gedi One Jam'. Additionally, the new variety is taller and naturally blooms two weeks earlier than the male parent variety, 'Gedi One Jam.'

In comparison to the commercially available variety 'Yomaggie' (U.S. Plant Pat. No. 11,855), 'Gedi Two Ama' has more ray florets which have a lighter purple color than the ray florets of 'Yomaggie.' Additionally, the inflorescence of the new variety is a spider-type compared to a quilleddaisy type of 'Yomaggie.' Further, the new variety has a more rounded plant form and blooms approximately two to three weeks earlier than plants of the commercially available variety 'Yomaggie.'

BRIEF DESCRIPTION OF THE PHOTOGRAPH

The photograph shows a plant of 'Gedi Two Ama.' One cutting was planted in the two-gallon container in May, and grown outdoors in Oxnard, Calif.

DETAILED BOTANICAL DESCRIPTION

In the following description, color references are made to The Royal Horticultural Society Colour Chart except where general terms of ordinary dictionary significance are used. The following observations and measurements describe 95 day old plants grown in Oxnard, Calif., during the month of September. Light conditions were bright, and no artificial shading was used. The humidity was low and no rainfall occurred. The growing temperature ranged from approximately 15° C. to 21° C. at night, and from approximately 19° C. to 32° C. during the day. Measurements and numerical values represent averages of typical flowering types.

Botanical classification: *Chrysanthemum morifolium* cultivar 'Gedi Two Ama'.
Commercial classification: Garden-type Chrysanthemum.

PROPAGATION

Time to rooting: Approximately 7 to 14 days at approximately 21° C.
Root description: Fine, fibrous.

PLANT

Growth habit: Mounding herbaceous perennial.
Height: Approximately 34 cm.
Plant spread: Approximately 56 cm.
Growth rate: Moderate.
Branching characteristics: Free branching.
Length of lateral branches: Approximately 31 cm.
Number of leaves per lateral branch: Approximately 125.
Age of plant described: Approximately 95 days.

FOLIAGE

Leaf:
- *Arrangement.*—Alternate.
- *Average length.*—Approximately 3 cm.
- *Average width.*—Approximately 2 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near Green 139A. Young foliage under side: Near Yellow-green 147B. Mature foliage upper side: Near Green 137A. Mature foliage under side: Near Yellow-green 147B. Venation upper side: Near Yellow-green 147C. Venation under side: Near Yellow-green 147B.
- *Venation type.*—Net.

Petiole:
- *Average length.*—Approximately 8 mm.
- *Color.*—Near Green 137A.
- *Diameter.*—Approximately 2 mm.
- *Internode length.*—Approximately 1.6 cm.

BLOOM

Inflorescence:
- *Flowering habit.*—Induced by darkness period greater than approximately 13.5 hours, approximately 42 days of appropriate day length required to induce and develop blooms.
- *Inflorescence form.*—Spider.
- *Flower fragrance.*—Not present.
- *Natural flowering season.*—Natural season flowering begins between September 1 and September 8 in Southern California.
- *Number of inflorescences per lateral branch.*—Approximately 45.
- *Inflorescence diameter.*—Approximately 5.6 cm.
- *Inflorescence depth.*—Approximately 1.7 cm.
- *Inflorescence longevity on plant.*—Approximately 23 days.
- *Persistence.*—Persistent.

Ray florets:
- *Appearance.*—Matte.
- *Texture.*—Smooth.
- *Average number per flower.*—Approximately 335.
- *Shape.*—Oblong.
- *Aspect.*—Cylindric.
- *Margin.*—Entire.
- *Apex.*—Rounded.
- *Length.*—Approximately 2.8 cm.
- *Width.*—Approximately 2 mm.
- *Color.*—Upper surface at first opening: Near Purple 75B. Upper surface at maturity: Near Purple 75C. Upper surface at fading: Near Purple 75D. Under surface at first opening: Near Purple 75B. Under surface at maturity: Near Purple 75C. Under surface at fading: Near Purple 75D.

Disc florets:
- *Appearance.*—Matte.
- *Texture.*—Smooth.
- *Average number per flower.*—Approximately 19.
- *Shape.*—Cylindric.
- *Apex.*—Obtuse.
- *Average length.*—Approximately 3 mm.
- *Average width.*—Approximately 1 mm.
- *Color.*—At first opening: Near Yellow-orange 14B. At maturity: Near Yellow-orange 15A. At fading: Near Yellow-orange 14A.

Peduncle:
- *Length.*—At terminal end (shortest): Approximately 3.9 cm. At lateral end (longest): Approximately 7.5 cm.
- *Angle to stem.*—Acute.
- *Strength.*—Moderate.
- *Color.*—Near Yellow-orange 147B.
- *Habit.*—Upright.
- *Diameter.*—Approximately 2.5 mm.
- *Texture.*—Lightly pubescent.

Inflorescence bud:
- *Length.*—Approximately 5 mm.
- *Diameter.*—Approximately 8 mm.
- *Form.*—Globular.
- *Color.*—Near Purple 76D.

Phyllaries (involucral bracts):
- *Appearance.*—Matte.
- *Texture.*—Lightly Pubescent.
- *Number.*—Approximately 30.

*Shape.*—Oblanceolate.
*Margin.*—Entire.
*Apex.*—Acute.
*Length.*—Approximately 7 mm.
*Width.*—Approximately 2 mm.
*Color.*—upper side: Near Green 138A. Under side: Near Green 138A.

REPRODUCTIVE ORGANS

Ray florets:
*Number of pistils per flower.*—1.
*Stigma shape.*—2 branched.
*Stigma color.*—Near Yellow 2B.
*Style color.*—Near Yellow-green 154D.
*Style length.*—Approximately 4 mm.
*Stamens: Absent.*

Disc florets:
*Number of pistils per flower.*—1.
*Stigma shape.*—2 branched.
*Stigma color.*—Near Yellow 2B.
*Style length.*—Approximately 2.5 mm.
*Style color.*—Near Yellow-green 154D.
*Number of stamens per flower.*—Approximately 5.
*Anther shape.*—Tubular.
*Anther color.*—Near Yellow 13A.
*Pollen color.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility has been observed.

Drought tolerance and cold tolerance: Neither resistance nor susceptibility has been observed.

What is claimed is:

1. A new and distinct cultivar of Chrysanthemum plant named 'Gedi Two Ama' as herein illustrated and described.

* * * * *